United States Patent
Nagano et al.

(10) Patent No.: US 6,887,477 B1
(45) Date of Patent: May 3, 2005

(54) METHOD OF TREATING ISCHEMIC DISEASE BY INTRAMUSCULAR ADMINISTRATION OF HEPATOCYTE GROWTH FACTOR

(76) Inventors: Tomokazu Nagano, c/o Sumitomo Pharmaceuticals Co., Ltd., 1-98, Kasugadenaka 3-chome, Konohana-ku, Osaka-shi, Osaka 554-0022 (JP); Ikue Kudo, c/o Sumitomo Pharmaceuticals Co., Ltd., 11, Kanda-surugadai 3-chome, Chiyoda-ku, Tokyo 101-8319 (JP); Takao Kawamura, c/o Sumitomo Pharmaceuticals Co., Ltd., 1-98, Kasugadenaka 3-chome, Konohana-ku, Osaka-shi, Osaka 554-0022 (JP); Mutsuo Taiji, c/o Sumitomo Pharmaceuticals Co., Ltd., 1-98, Kasugadenka 3-chome, Konohana-ku, Osaka-shi, Osaka 554-0022 (JP); Hiroshi Noguchi, c/o Sumitomo Pharmaceuticals Co., Ltd., 11, Kanda-surugadai 3-chome, Chiyoda-ku, Tokyo 101-8319 (JP); Shunsuke Tani, c/o Sumitomo Pharmaceuticals Co., Ltd., 2-8, Doshomachi 2-chome, Chuo-ku, Osaka-shi, Osaka 541-8510 (JP); Hiroo Maeda, c/o Sumitomo Pharmaceuticals Co., Ltd. 3-45, Kurakakiuchi 1-chome, Ibaraki-shi, Osaka 567-0878 (JP)

(*) Notice: Subject to any disclaimer, the term of this patent is extended or adjusted under 35 U.S.C. 154(b) by 0 days.

(21) Appl. No.: 09/762,188
(22) PCT Filed: Aug. 4, 1999
(86) PCT No.: PCT/JP99/04249
  § 371 (c)(1),
  (2), (4) Date: Feb. 5, 2001
(87) PCT Pub. No.: WO00/07615
  PCT Pub. Date: Feb. 17, 2000

(30) Foreign Application Priority Data
  Aug. 5, 1998 (JP) ............................................. 10-222170
  Jan. 13, 1999 (JP) ............................................. 11-006261

(51) Int. Cl.[7] .......................... A61K 38/00; A61K 38/18; C07K 14/00
(52) U.S. Cl. ...................... 424/198.1; 424/85.1; 514/2; 514/12; 530/300; 530/350; 530/399
(58) Field of Search .................. 514/2, 12; 530/300, 530/350, 351, 399; 424/85.1, 184.1, 198.1

(56) References Cited

U.S. PATENT DOCUMENTS 5,837,676 A * 11/1998 Goldberg et al. ............... 514/8
6,133,231 A * 10/2000 Ferrara et al. .................. 514/2
6,436,388 B2 * 8/2002 Kudo et al. ................ 424/85.1
6,472,366 B2 * 10/2002 Kishino et al. ................. 514/2
6,498,144 B1 * 12/2002 Goldberg et al. .............. 514/12

FOREIGN PATENT DOCUMENTS

| JP | A597694 | 4/1993 |
| JP | A6340546 | 12/1994 |
| JP | A7300426 | 11/1995 |
| JP | A8295634 | 11/1996 |
| WO | A1-9303061 | 2/1993 |

OTHER PUBLICATIONS

Pettit et al. The development of site–specific drug–delivery systems for protein and peptide biopharmaceuticals. Trends in Biotech 16: 343–349, 1998.*
Pu et al. Enhanced revascularisation after angiogenic stimulation in a rabbit model of bilateral limb ischaemia. Eur J Vasc Endovasc Surg. 9(2):189–196, 1995.*
Pu et al. Angiogenic growth factor and revascularization of the ischemic limb: evaluation in a rabbit model. J Surg Res. 54(6):575–583, 1993.*
Uematsu Y et al. Effective administration route for the deleted form of hepatocyte growth factor To exert its pharmacological effects. J Pharm Sci. ;88(1):131–135, 1999.*
Takeshita et al. Intramuscular administration of vascular endothelial growth factor induces dose–dependent collateral artery augmentation in a rabbit models of chronic limb ischemia. Circulation. 90:II228–234, 1994.*
Baffour et al. Enhanced angiogenesis and growth of collaterals by in vivo administration of recombinant bFGF in a rabbit model of acute lower limb ischemia: dose–response effect of basic fibroblast growth factor. J Vasc Surg 16(2): 181–191, 1992.*
Taniyama et al. Therapeutic angiogenesis induced by human hepatocyte growth factor gene in rat and rabbit hindlimb ischemia models: preclinical study for treatment of peripheral arterial disease. Gene Therapy 8: 181–189, 2001.*
Morishita et al. Therapeutic angiogensis induced by human recombinant hepatocyte growth factor in rabbit hind limb ischemia model as cytokine supplement therapy. Hypertension 33: 1379–1384, 1999.*
Schaper et al. Is hepatocyte growth factor a protein with cardioprotective activity in the ischemic heart? Circulation 95: 2471–2472, 1997.*
Yamaguchi et al., Japanese Circulation Journal, vol. 62, Supp. I, p. 407 (1998).
Van Belle et al., Circulation, vol. 97, No. 4, pp. 381–390 (1998).

* cited by examiner

Primary Examiner—Elizabeth C Kemmerer
Assistant Examiner—Bridget E. Bunner
(74) Attorney, Agent, or Firm—Birch, Stewart, Kolasch & Birch, LLP (57) ABSTRACT

Preparations to be administered for treating or preventing ischemic diseases or arterial diseases which contain Hepatocyte growth factor (HGF) as an active ingredient. The preparations provide such effect that HGF concentration in an affected region to which HGF was administered is maintained, a half-life is longer, a dose can be reduced, and other organs except the affected region are less affected in comparison with intravenous administration.

3 Claims, 7 Drawing Sheets

1: NON-TREATED,
2: 5 MIN AFTER ADMINISTRATION OF 0.03 mg/kg HGF,
3: 30 MIN AFTER ADMINISTRATION OF 0.03 mg/kg HGF,
4: 5 MIN AFTER ADMINISTRATION OF 0.3 mg/kg HGF,
5: 30 MIN AFTER ADMINISTRATION OF 0.3 mg/kg HGF,
6: 5 MIN AFTER ADMINISTRATION OF 3 mg/kg HGF,
7: 30 MIN AFTER ADMINISTRATION OF 3 mg/kg HGF,
PY: BLOTTING BY ANTI-PHOSPHOTYROSINE ANTIBODY
c-Met: BLOTTING BY ANTI-c-Met ANTIBODY
ARROWS SHOW LOCATIONS OF c-Met.

METHOD OF TREATING ISCHEMIC DISEASE BY INTRAMUSCULAR ADMINISTRATION OF HEPATOCYTE GROWTH FACTOR

This application is the national phase under 35 U.S.C. § 371 of PCT International Application No. PCT/JP99/04249 which has an international filing date of Aug. 4, 1999, which designated the United States of America.

TECHNICAL FIELD

The present invention relates to preparations to be administered for treating or preventing ischemic diseases or arterial diseases which contain Hepatocyte growth factor (HGF) as an active ingredient. More particularly, the invention relates to preparations administered intramuscularly for treating or preventing ischemic diseases or arterial diseases of the heart or extremities by administration to an affected part and local muscular region around it.

BACKGROUND ART

Hepatocyte growth factor (HGF) is discovered as a potent proliferation promoting factor for mature hepatocytes, and is a protein whose gene has been cloned by gene cloning (Biochem Biophys Res Commun, 122, 1450 (1984); Proc. Natl. Acad. Sci. USA, 83, 6489, (1986); FEBS Letter, 22, 231 (1987); Nature, 342, 440 (1989); Proc. Natl. Acad. Sci. USA, 87, 3200 (1991)). Subsequent studies have been proving that HGF functions as a liver regenerating factor in vivo for restoring and regenerating a damaged liver, and also has an angiogenic effect, playing a significant role in treating or prevention of ischemic and arterial diseases (Symp. Soc. Exp. Biol., 47 cell behavior, 227–234 (1993); Proc. Natl. Acad. Sci., 90; 1937–1941 (1993); Circulation, 97, 381–390 (1998)). In other words, it was reported that significant angiogenesis was observed, and the blood flow was improved, reduction of the blood pressure was inhibited and symptoms of ischemia were improved as a result, when HGF is administered to a rabbit model of hindlimb ischemia. Because of such reports, it is considered today that HGF expresses and functions as one of angiogenic factors.

Thus, HGF has various functions including that of an angiogenic factor, and different attempts have been made for utilizing it as a drug However, the half-life of HGF in the blood has been a problem. The half-life of HGF is as short as about 10 min so that it was difficult to maintain a concentration in the blood, and transportation of an effective dose to an affected region was also a problem.

In the case of protein preparations in general, it is commonly known that intravenous administration is often employed. Regarding administration of HGF to the ischemic disease model described above, examples of intravenous and intra-arterial administration, for example, were illustrated (Circulation, 97, 381–390 (1998)). Although the effectiveness of HGF to ischemic or arterial diseases have been shown, no conclusion has been made specifically with regard to an effective method of administration or dose of HGF. In the case of HGF, in particular, because there are such problems of the half-life and transportation to an affected region as described, no conclusion has been made regarding an effective method of administration or dose of HGF.

It is an object of the invention to provide preparations to be administered for treating or preventing ischemic diseases or arterial diseases which contain HGF as an active ingredient. More particularly, the invention relates to preparations administered intramuscularly for treating or preventing ischemic diseases or arterial diseases of the heart or extremities by administration to an affected part and local muscular region around it. The preparation for intramuscular administration according to the invention is directly administered intramuscularly to an ischemic region of the heart or extremities that represents a damaged region, for example, and an efficiency of utilization of HGF administered is very high, so that a dose can be reduced in comparison with the case of intravenous administration. In addition, because transpiration, distribution and effect from the region to which the preparation is administered to the blood and the whole body excluding muscular tissues and peripheral tissues of the region is low, it is effective in such manner that an effect to other organs can be reduced, and it provides a higher selectivity.

For adapting HGF to ischemic or arterial diseases, the inventors studied hard about a dose and a method of administration. Such methods as intravenous bolus administration, intravenous continuous administration, subcutaneous administration, intraperitoneal administration and intramuscular administration have been considered and studied as methods of administration of HGF for the above-described diseases.

As described above, in the case of protein preparation in general, it is commonly known that the intravenous administration is often employed, and it has been a common knowledge that it is effective to allow a drug to act from inside a blood vessel, because ischemic and arterial diseases are angiopathy. Consequently, as for administration of HGF to ischemic and arterial disease models, intravenous or intra-arterial administration was employed in most examples, information including literature about intramuscular administration of HGF was scarce, and no report on intracorporeal kinetics of HGF could be found. Thus, no report was found regarding an attempt of intramuscular administration of HGF to an ischemic or arterial disease model, and hitherto it has never been clarified, therefore, whether intramuscular administration of HGF is effective or not.

The inventors studied pharmacokinetics of HGF administered intramuscularly to an ischemic region of hindlimb in comparison with that administered through another route (intravenous administration) by using rats. As a result, in the case of the intramuscular administration, it was found that HGF administered was maintained at a very high concentration in the region to which it was administered, and transportation to serum, liver and kidney was low compared to the case of intravenous administration. Additionally, similarly to the case of intramuscular administration, when HGF was subcutaneously administered, HGF was maintained at a high concentration in the region to which it was administered, and transportation from the region to the circulating blood was low.

On the other hand, in the case HGF was administered intravenously, it was found that HGF was at a low concentration in a muscle, while it was maintained at a high concentration in the blood. Accordingly, it was recognized for the first time that an efficiency was low in the intravenous administration, and it was effective to directly administer HGF intramuscularly to an affected region or an area thereof, when it was intended to allow HGF to act to an ischemic region and a muscle or a blood vessel present therein.

Further, as a result of comparison between intramuscular administration and intravenous bolus administration of HGF, it was found that the maximum concentration in the blood, liver and kidney in the case of intramuscular administration was a hundredth or less, more preferably a thousandth or less of that in the intravenous bolus administration. Moreover, it was found that the concentration in muscular tissues of an administration region in the case of intramuscular administration was 50 times or more, more preferably 200 times or more of that in the intravenous bolus administration.

Furthermore, as a result of comparison of the AUC in the blood, liver and kidney between intramuscular administration and intravenous bolus administration, it was found that the AUC in the blood, liver and kidney in the case of intramuscular administration was a fifth or less, more preferably a tenth or less of that in the intravenous bolus administration. In addition, the AUC in muscular tissues of an administration region in the case of intramuscular administration was 50 times or more, more preferably 200 times or more of that in the intravenous administration.

As described, because it was found that HGF was maintained at a high concentration in an administration region of affected area, it was succeedingly examined whether HGF in the muscular tissues was transported to tissues and blood vessels in the affected area, and really provided its efficacy as HGF. In other words, the function of HGF was confirmed by using, as an index, presence or absence of phosphorylation of c-Met that is a receptor of HGF. As a result, when HGF of 30 to 3000 $\mu$g/kg was administered intramuscularly to rats, it was found that a Tyr residue of c-Met (a receptor of HGF) was phosphorylated and activated in muscular tissues, while no activation of c-Met was observed in tissues of the liver and kidney in comparison with those of non-administration group. It means that HGF provides an effect in muscular tissues to which it is administered, while it provides no effect in the liver and kidney.

Since the effect of HGF was confirmed as described above, the inventors studied practically an efficacy of HGF by intramuscular administration by using an animal model of arteriosclerosis obliterans (ASO). Specifically, by using rat model of hindlimb ischemia, it was studied how ischemic damages of the hindlimb could be improved by the above-described intramuscular administration of HGF. As a method of study, a surface temperature of skin of the hindlimb was measured by using a thermography, and effectiveness of the intramuscular administration was confirmed by using, as an index, inhibition of reduction of the surface temperature of skin. As a result, it was found that reduction of the surface temperature of skin in the hindlimb ischemia was suppressed by the intramuscular administration. It shows that the blood circulation in the hindlimb ischemia was improved by angiogenic effect of HGF, and reduction of the temperature was accordingly suppressed.

Thus, the effectiveness of intramuscular administration of HGF to ASO models was proved for the first time.

The inventors further studied the I/N ratio (%) (blood pressure in an ischemic limb/blood pressure in a normal limb×100) by the intramuscular administration, using rat ASO model of hindlimb ischemia and rabbit ASO model of hindlimb ischemia. As a result, significant improvement of the I/N ratio was observed at a low dose and a low administration frequency. It shows that the blood circulation in the ischemic limb was improved by the angiogenic effect of HGF. Further, by an angiographic study of the rabbit model, an increase rate of the angiographic score was significantly higher in the HGF administration group. It shows that development of collateral vessels was accelerated by the effect of HGF. By also studying arthrosclerosis in the ischemic limb, presence or absence of necrosis and auto-amputation of the toe and ulceration in the crus of ischemic limb, tendency of improvement by the intramuscular administration of HGF was observed.

Thus, it was proved that intramuscular administration of HGF was very effective to ischemic diseases.

Confirmation of the effectiveness by using the thermography as the results of the experiments means that the intramuscular administration of HGF is also effective for clinical patients with ASO, particularly, those with cold sense in an ischemic limb as an subjective symptom from a minor stage, and confirmation of the recovery accelerating effect by the I/N ratio and angiography and such improving effect as relief of symptoms in the ischemic limb show that treatment by the intramuscular administration of HGF is effective to patients with ASO of an early to major stages. It enables treatment of ASO in a minor stage before it progresses to a major stage of ASO that requires amputation of a hindlimb due to ischemia, and preparations for the intramuscular administration according to the invention is capable of providing an epoch-making treatment for a lot of patients with ASO of minor stage that cannot be effectively treated today, enabling prohibition of progress of symptoms, improvement thereof and recovery therefrom. Also, they provides a drug providing an efficacy at a low dose, and less affecting other organs except an affected region in comparison with those for intravenous administration.

It was also found that HGF preparations preferably contain no proteoglycans constituting such extracellular matrix as chondroitin sulfate and protein carriers containing them as an ingredient in order to further promote such effect of HGF as described above. In other words, as a result of studying an effect of containment of chondroitin sulfate on release of HGF from a minipellet that was prepared by using collagen as a ground substance, it was found that HGF was released at a higher rate from a minipellet containing HGF with chondroitin sulfate in comparison with that with alanine instead of chondroitin sulfate. It shows that HGF is released at a lower rate in HGF preparations containing no proteoglycans that constitute such extracellular matrix as chondroitin sulfate. It means that HGF preparations containing no proteoglycans that constitute such extracellular matrix as chondroitin sulfate can be more easily retained in local tissues to which it is administered, and transportation and distribution to other organs of the body through the intermediary of the blood can be reduced.

SUMMARY OF THE INVENTION

The present invention has been achieved on the basis of the above-described findings. Thus, the invention relates to:

(1) a preparation containing HGF as an active ingredient, and allowing an effective amount of the factor to be transported to, distributed in, and act on local tissues of a region to which it is administered and tissues around the region, while it reduces transportation, distribution and effect of the factor to the blood and other organs of the body except the region to which it is administered;

(2) the preparation according to aspect (1) for use in treating and preventing ischemic and arterial diseases;

(3) the preparation according to aspect (1) or (2) used for intramuscular administration, in which the region to which it is administered is a muscle;

(4) the preparation according to aspect (1) or (2) for subcutaneous administration or external application or in the form of a cataplasm, in which the region to which it is administered is subcutaneous or intraepidermal;

(5) the preparation according to aspect (3) for intramuscular administration, in which the region to which it is administered is a skeletal or cardiac muscle;

(6) the preparation according to aspect (1), (2), (3) or (5), in which its transportation to, distribution in and action on muscular tissues representing the region to which it is administered surpass its transportation to, distribution in and action on the blood, liver and kidney;

(7) the preparation according to aspect (1), (2), (3), (5) or (6) for intramuscular administration, in which the maximum concentration in the blood, liver and kidney is a hundredth or less, and a concentration in muscular tissues representing the region to which it is administered is 50 times or more in comparison with the case the same dose of the preparation containing HGF as an active ingredient is administered by intravenous bolus administration;

(8) the preparation according to aspect (1), (2), (3), (5) or (6) for intramuscular administration, in which AUC in the blood, liver and kidney is a fifth or less, and AUC in muscular tissues representing the region to which it is administered is 50 times or more in comparison with the case the same dose of the preparation containing HGF as an active ingredient is administered by intravenous bolus administration;

(9) the preparation according to aspect (1), (2), (3), (5), (6), (7) or (8) for intramuscular administration for treating or preventing ischemic or arterial diseases of the heart or extremities;

(10) the preparation according to aspect (9) for intramuscular administration for treating or preventing ischemic or arterial diseases of the heart or extremities, in which the region to which it is administered is a local muscle of an affected region and around it;

(11) the preparation according to aspect (1), (2), (3), (5), (6), (7), (8), (9) or (10) for intramuscular administration, in which a dose is at 0.01 to 500 μg/kg;

(12) the preparation according to aspect (11), in which the dose is at 0.1 to 10 μg/kg;

(13) the preparation according to any one of aspects (1) to (12), in which the arterial diseases are arteriosclerosis obliterans;

(14) the preparation according to any one of aspects (1) to (12), in which the ischemic diseases are ischemic heart diseases; and (15) the preparation according to any one of aspects (1) to (14), in which the preparation contains HGF as an active ingredient, and does not contain any substance that binds and adsorbs HGF.

BEST MODE FOR CARRYING OUT THE INVENTION

HGF used in the invention is a known substance, any compounds prepared by various methods can be used if they are purified to an extent that they may be used as a medicine, or any commercial products can be used (for example, Toyobo Code No. HGF-101). To prepare HGF, for example, primary culture cells or a cell line which produce(s) HGF are cultivated, and HGF is obtained by isolating from the culture supernatant and purifying. Or by gene engineering technique, a gene encoding HGF is inserted into a proper vector, and it is incorporated into a proper host to transform, and a desired recombinant HGF is obtained from the culture supernatant of this transformant (for example, Nature, 342, 440, 1989; Japanese Laid-open Patent No. 5-111383; Biochem. Biophys. Res. Commun. 163, 967, 1989). The host cell is not particularly limited, and various host cells conventionally used in gene engineering technique may be used, which are, for example, *Escherichia coli*, yeast, and animal cells. Thus obtained HGF is not limited as far as it has substantially the same action as the natural HGF, and for example, one or plural amino acids in the amino acid sequence may be replaced, deleted and/or added, or similarly sugar chain may be replaced, deleted and/or added.

The preparation containing HGF according to the invention is characterized in that it allows an effective amount of the factor to be transported to, distributed in and act on local tissues of a region to which it is administered and tissues around it, while it brings about reduction of the factor to be transported to, distributed in, and act on the blood and other organs of the body except the region to which it is administered.

As for particularly applicable diseases, all diseases of the circulating system are included, for example, ischemic or arterial diseases to which the efficacy of HGF has already been confirmed. Specifically, heart diseases include ischemic heart diseases, cardiac infarction, acute cardiac infarction, cardiomyopathy, angina pectoris, unstable angina pectoris, coronary arteriosclerotic disease and cardiac failure, and ischemic diseases of extremities include arteriosclerosis obliterans, Buerger disease, vascular damage, arterial embolism, arterial thrombosis, arterial obliteration of organs and aneurysm.

As for a method of administration, any administration method may be employed, provided, as described above, that HGF of an effective dose can be transported to, distributed in and act on local tissues of a region to which it is administered and tissues around the region, and transportation to, distribution in and action on the blood and other organs of the body except the region to which it is administered can be reduced. Specifically, intramuscular (skeletal muscle, cardiac muscle) administration, subcutaneous or intraepidermal administration are included. Pharmaceutical forms include, for example, aqueous or oleaginous solutions for injection, ointments, creams, lotions, aerosols and cataplasms. Further, a sustained-release minipellet can be prepared, and buried in the vicinity of an affected region, or the preparation can be gradually administered to an affected region in a continuous manner by using an osmotic pump. Such preparations can be prepared by using a technique known in the art, and a pH regulator, buffer, stabilizer, preservative or solubilizing agent may be added to HGF that is an active ingredient, if it is required.

In such case, it is preferable that the preparation containing HGF according to the invention contain no substance that binds and adsorbs HGF. In other words, the preparation containing HGF presented for the first time in the invention with no such component of extracellular matrix as chondroitin sulfate is characterized in that HGF is slowly released from a region to which it is administered in comparison with that with such component. Therefore, transportation of a high amount of HGF from the local region of administration to other organs can be restricted. Further, although it is known that the blood clearance can be restricted by adding heparin that is a component of extracellular matrix as well as chondroitin sulfate (Hepatology, 20, 417 (1994)), since the preparation according to the invention contains no such component of extracellular matrix, the clearance of HGF transported to the blood may not be restricted. Therefore, it is considered that transportation and reaction to other organs can be further reduced, and the efficacy in a muscle representing a region of administration can be increased.

Now, substances adsorbing and binding HGF include sugar, glycoprotein, glycolipid and conjugated sugar that are components of extracellular matrix. More specifically, they include chondroitin sulfate, heparan sulfate, heparin, heparin-like substances. Sugar, glycoprotein, glycolipid and conjugated sugar that contains a sulfate are also substances that bind and adsorb HGF. In addition, unlimitedly to biological component, such substances containing a part of sugar, glycoprotein, glycolipid and conjugated sugar also bind and adsorb HGF. Furthermore, as substances adsorbing and binding HGF, such protein carriers as protein and glycoprotein used in protein preparations or those contained therein that adsorb and bind HGF are also included. Substances binding and adsorbing HGF that are minutely contained in a protein carrier are included in this category. The preparation containing HGF according to the invention preferably contains no such substances that bind and adsorb HGF as described above.

It is known that such physical property as a rate of polymerization of protein comes to be different in a protein preparation according to such conditions as pH, ionic strength and ion concentration or chemical modification. It is considered that such difference in physical property of protein also affect retention in such tissues as a muscle in an administration region and transportation to the blood of a preparation for the administration according to the invention.

As shown in Examples described below, the preparation for the administration according to the invention is also characterized in that it can be used at a low dose. The preparation can be administered at a dose described below, although it depends on symptoms, age and sex of a patient.

Specifically, considering that 1) the preparation was confirmed to be effective at a dose of 1 $\mu$g/kg in Examples, 2) an effective dose for human being is assumed to be about 0.2 $\mu$g/kg, when a dose (per body weight) confirmed to be effective for a rat in Examples is converted to a dose per surface area of body, and 3) common technical knowledge of those in the art, the dose of preparation according to the invention is at least 500 $\mu$g/kg/time or less, specifically, 0.01 to 500 $\mu$g/kg/time, preferably, about 0.1 to 10 $\mu$g/kg/time. As for a period and frequency of administration, a frequency of once to twice a week for a period of three months at the longest, preferably less than seven times a week for a period of a week or less, more preferably once or twice a week for a period of a week or less can be used.

As for methods of identification of a region of administration and administration in a patient to whom the preparation for the administration according to the invention is applied, such methods as described below can be used. For example, in diagnosis of ischemia due to arteriosclerosis obliterans in a limb, an ischemic limb and a region thereof should be estimated by rest pain, intermittent claudication and presence or absence of ulcer, and also by measuring an ambulant distance by using a treadmill and the ankle pressure index (the ratio between the blood pressures of a hindlimb and a brachium) by using a Doppler hemodynamometer or the like. By means of the angiography using a contrast medium, digital subtraction angiography or magnetic resonance angiography, a region constricted or obliterated of a blood vessel is identified in detail. Regarding determinination of a state of limb, for example, a standard procedure recommended by the Society for Vascular Surgery/North American Chapter and International Society for Cardiovascular Surgery should be followed. The preparation for the administration according to the invention is then administered to muscles in the ischemic region identified by the angiography or the like and those in the vicinity thereof dividedly at one to twenty locations, preferably three to six locations according to the size of the region.

The preparation for intramuscular administration according to the invention can be used for preventative purposes in addition to treating purposes.

EXAMPLES

Although the invention is described below in detail by way of Examples, the invention is not limited in any manner to such Examples.

Example 1

Comparison of Pharmacokinetics of HGF by Administration Routes

1. Study of Pharmacokinetics of HGF by Intramuscular Administration (1) Method

Using Fischer rats, concentrations of HGF in the serum, liver, kidney and muscles (an administration area and a contralateral side thereto) were measured after intramuscular administration of HGF at doses of 0.3, 1 and 3 mg/kg and continuous intravenous administration thereof for 3 hrs at doses 6, 60 and 600 μg/kg/hr. The intramuscular administration was conducted in a central part of an posterior muscle of left thigh of the rats under ether anesthesia. A dose of 1 mL/kg was used, and 10 mM citrate buffer (pH 5.5) containing 0.3 M NaCl, 0.03% Tween 80 and 5 mg/mL L-alanine was used as a vehicle. After 5 min, 30 min, 2 hrs, 8 hrs and 24 hrs of the administration of HGF, the serum, left lobe of liver, kidney and muscles (the administration area and the contralateral side thereto) were harvested from the rats. The continuous intravenous administration was conducted through the tail vein of the rats, and an administration rate was at 0.07 mL/hr. In 3 hrs or more after commencement of the administration, the serum, left lobe of liver, kidney and muscles were similarly harvested. Concentration of human HGF in the serum and tissue was measured by using Immunis HGF EIA (prepared by Institute of Immunology) that is a ELISA kit for measuring human HGF. As for HGF in the organs, 20 mM Tris-HCl (pH 7.5) containing 2 M NaCl, 1 mM PMSF, 1 mM EDTA and 0.1% Tween 80 was used as an extraction buffer (muscles: 12 mL/g tissue, liver and kidney: 8 mL/g tissue), homogenized for a minute, and centrifuged for 60 min at 4° C. and 15,000 rpm, and an amount of HGF in the extraction buffer was measured by using the ELISA kit described above. As for a standard solution, HGF of a known concentration was also added to tissue of rats that were not subjected to the administration of HGF, and a solution containing HGF that was extracted in a similar manner was used. Regarding a sample diluent as well, an extraction buffer for the tissue of rats that were not subjected to the administration of HGF was similarly prepared for use. An analysis of change in concentration was conducted by using the moment analysis method.

(2) Result

Figure 1:
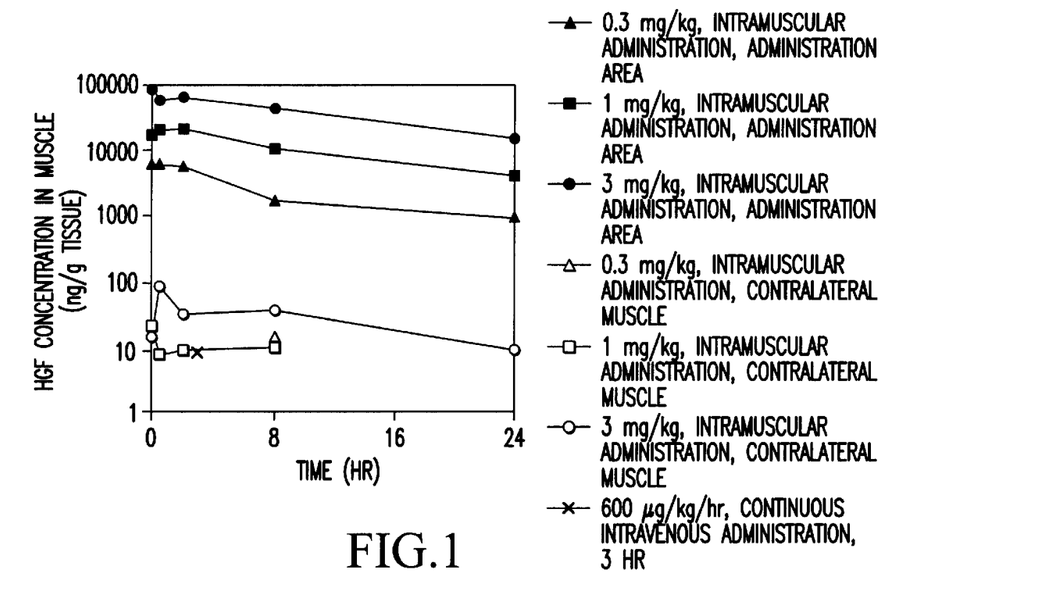
FIG. 1 is a figure showing change in intramuscular concentration of HGF after administration of HGF to a posterior femoral muscle of a rat.

Change in concentration of HGF in the muscles after the intramuscular administration of HGF to the femoral region is shown in FIG. 1. A result obtained by the continuous intravenous administration of HGF to the tail vein is also shown in FIG. 1. The concentration in the muscles after 3 hrs of continuous administration of HGF at 6 and 60 μg/kg/hr through the tail vein was below the measurable limit (1.5 ng/g tissue). Pharmacokinetic parameters in the muscles in the intramuscular administration of 3 mg/kg are shown in Table 1. It was found that $t_{1/2}$ of HGF in the muscles of region of administration was 10.6 hrs, and a concentration of about 18% of the maximum concentration was maintained even after 24 hrs of the administration. In the case HGF was administered through the tail vein by means of intravenous bolus administration, an HGF concentration detected in the muscles was in the order of 10 ng/g tissue when HGF was administered at a dose of 0.3 mg/kg, for example.

TABLE 1

| Administration route, dose | Intramuscular administration, 3 mg/kg | |
| --- | --- | --- |
| Muscular region | Administration area | Contralateral side |
| AUC (hr·ng/g tissue) (infinite) | $11.6 \times 10^5$ | 820 |
| $t_{1/2}$ (hr) | 10.6 | 11.2 |
| Cmax (ng/g tissue) | $84.1 \times 10^8$ | 82.4 |
| Tmax | 5 min | 5 min |

In Table 1, the contralateral side is an area corresponding to the administration area in the opposite side thereof. In other words, because the administration was at a posterior muscle of a left thigh, it is a posterior muscle of right thigh opposite thereto.

Figure 2:
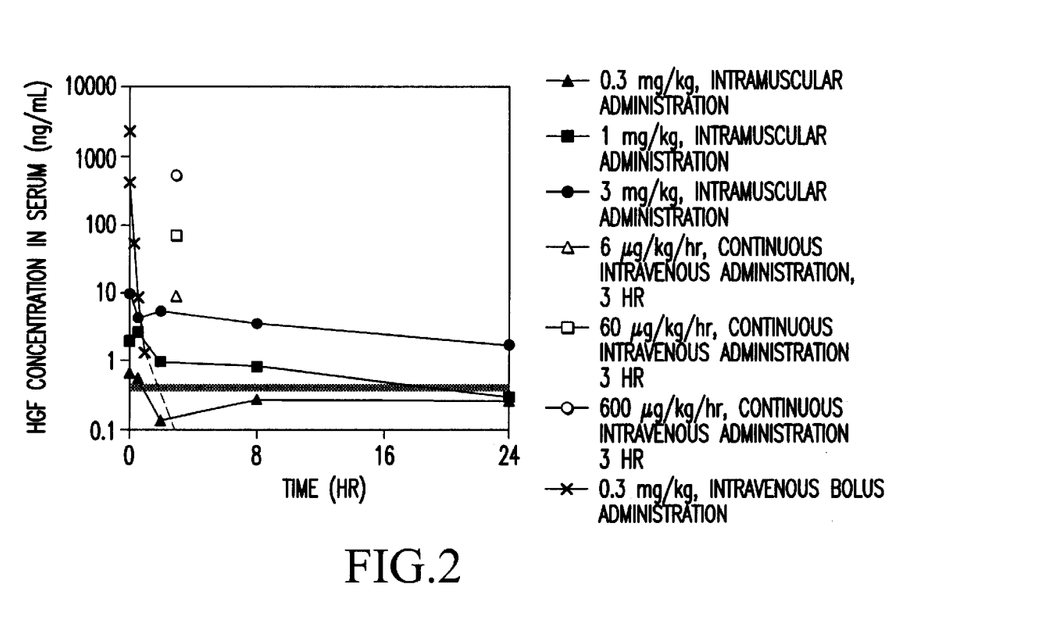
FIG. 2 is a figure showing change in concentration of HGF in the serum after administration of HGF to a muscle of femoral region of a rat.
Figure 3:
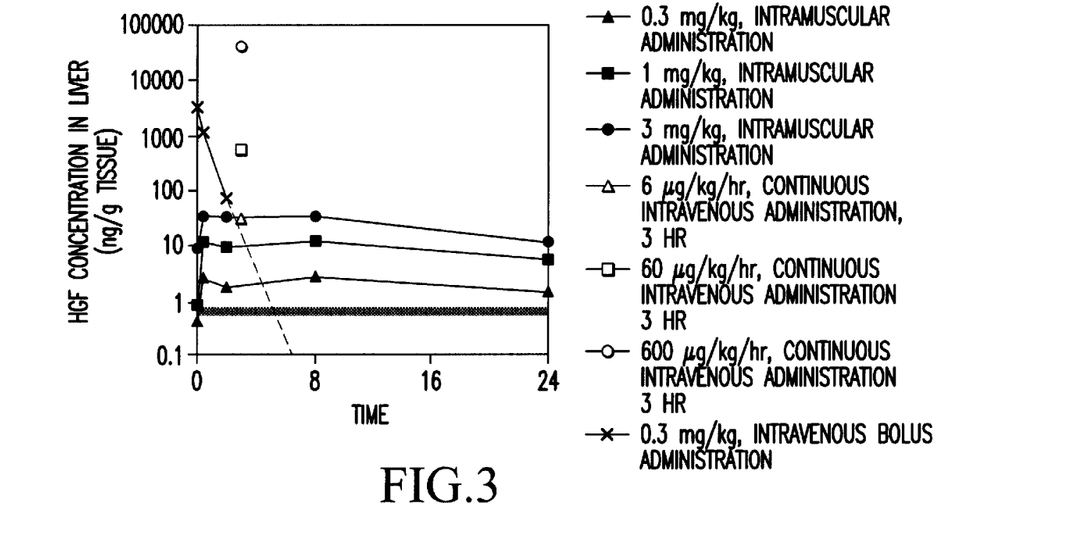
FIG. 3 is a figure showing change in concentration of HGF in the liver after administration of HGF to a muscle of femoral region of a rat.
Figure 4:
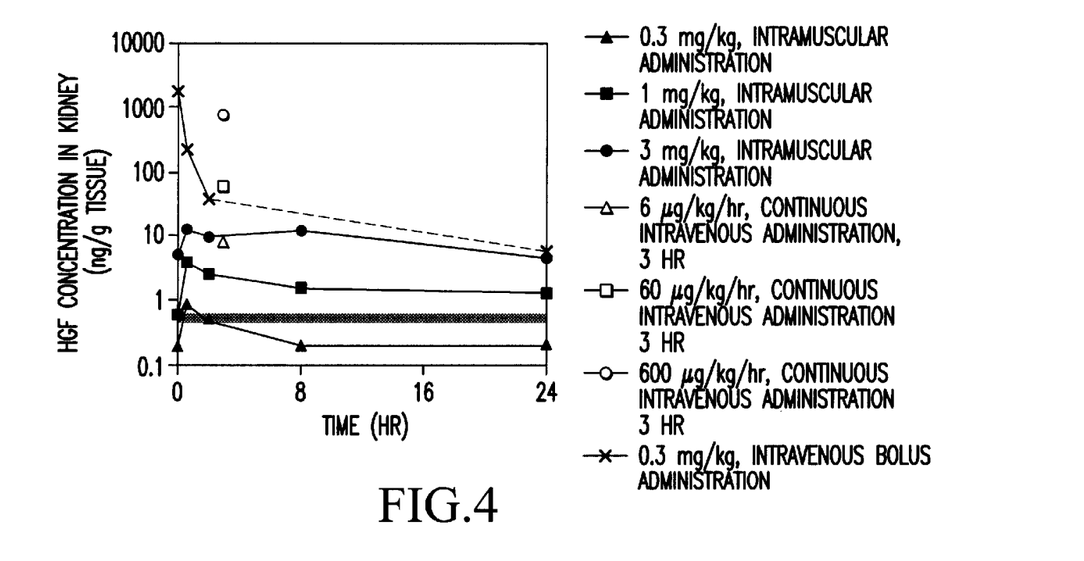
FIG. 4 is a figure showing change in concentration of HGF in the kidney after administration of HGF to a muscle of femoral region of a rat.

As shown in FIG. 1 and Table 1, in the case of the intramuscular administration of HGF, the concentrations were very high in the muscle to which it was administered. It was considered that the concentrations were more than sufficient for HGF to demonstrate its efficacy. On the other hand, in the muscles of contralateral side, it was about 1/1000 of the concentration in the administration area. As shown in FIG. 2, when HGF was intramuscularly administered, an HGF concentration in the serum was maintained relatively in a low level, and transportation from the muscles of administration area to the circulating blood was as low as 6.7%. Further, as shown in FIGS. 3 and 4, when HGF was administered intramuscularly, HGF concentrations in the liver and kidney were significantly low in comparison with those in the case of the intravenous administration. A result of HGF concentrations in the serum, liver and kidney after continuous intravenous administration of HGF is also shown in FIGS. 2, 3 and 4.

In the case of continuous intravenous administration of HGF, HGF concentrations in the serum, liver and kidney were maintained in a high level, while an HGF concentration in the muscles was significantly low. In an administration group of 600 μg/kg/hr, that is, the highest dose, while HGF of 536 ng/mL was present in the serum, it was less than 10 ng/g tissue in the muscles. It was considered from the fact that the intravenous administration is less efficient for allowing HGF to selectively act on an affected muscular region with ischemia and muscles around it or blood vessels present therein, and direct administration to a local muscle is more effective. In addition, it was considered that HGF can be allowed to selectively act on muscular tissues without affecting other regions by intramuscular administration thereof 2. Comparison of Change in HGF Concentration in the Blood by Administration Routes (1) Method By using Fischer rats, concentrations of HGF in the serum was measured after intramuscular administration of HGF at a dose of 3 mg/kg, intravenous bolus administration at a dose of 0.3 mg/kg and subcutaneous administration at a dose of 3 mg/kg. The intramuscular administration was conducted in a central part of an posterior muscle of left thigh of the rats under ether anesthesia. A dose of 1 mL/kg was used, and 10 mM citrate buffer (pH 5.5) containing 0.3 M NaCl, 0.03% Tween 80 and 5 mg/mL L-alanine was used as a vehicle. In the intramuscular administration, the serum was harvested from the rats after 5 min, 30 min, 2 hrs, 8 hrs and 24 hrs of the administration of HGF. The intravenous administration was conducted through the tail vein of the rats, and the serum was harvested after 2 min, 5 min, 15 min, 30 min, 1 hr, 2 hrs, 3 hrs, 12 hrs and 24 hrs of the administration. In the subcutaneous administration, the serum was harvested after 5 min, 15 min, 30 min, 1 hr, 2 hrs, 5 hrs, 12 hrs and 24 hrs of the administration. A human HGF concentration in the serum of rats was measured by using Immunis HGF EIA (prepared by Institute of Immunology) that is an ELISA kit for measuring human HGF. An analysis of change in concentration was conducted by using the moment analysis method.

(2) Result

Pharmacokinetic parameters obtained by the analysis of results of measurements are shown in Table 2. In the case of the intravenous bolus administration, however, it should be noted that parameters were calculated for the administration of HGF at 3 mg/kg by assuming a linearity in relation to the doses. AUC in the serum was low in the intramuscular and subcutaneous administrations in comparison with the intravenous bolus administration, and was, respectively, at 6.7% and 2.6% of that in the intravenous bolus administration. The maximum concentration (Cmax) in the serum was also low in the intramuscular and subcutaneous administrations in comparison with that in the intravenous bolus administration, and was, respectively, at 0.012% and 0.0087% of C0 in the intravenous bolus administration.

TABLE 2

| Administration route<br>Dose | Intramuscular<br>3 mg/kg | Intravenous<br>bolus<br>3 mg/kg | Subcutaneous<br>3 mg/kg |
|---|---|---|---|
| AUC (min•ng/ml) (infinite) | 6310 | 94390 | 2419 |
| t½ (min) | 801 | 8.8 | 525 |
| Cmax or C0 (ng/ml) | 8.96 | 73380 (C0) | 6.42 |
| Tmax | 5 min | — | 5 min |
| AUC ratio (% i.v.) | 6.7% | — | 2.6% |
| Cmax ratio (% i.v. C0) | 0.012% | — | 0.0087% |

3. Comparison of Change in HGF Concentrations in Muscles by Administration Routes (1) Method By using SD rats, concentrations of HGF in muscles were measured by intramuscular administration of HGF at a dose of 0.01 mg/kg and intravenous bolus administration at a dose of 30 mg/kg. The intramuscular administration was conducted in a central part of a posterior muscle of left thigh of the rats under ether anesthesia. A dose of 0.5 mL/kg was used, and 10 mM citrate buffer (pH 5.5) containing 0.3 M NaCl, 0.03% Tween 80 and 5 mg/mL L-alanine was used as a vehicle. After 30 min, 6 hrs and 24 hrs of the administration of HGF, muscles (administration area) were harvested from the rats. The intravenous bolus administration was conducted through the tail vein of the rats at a dose of 1 mL/kg, and the muscles were harvested in a similar manner after 5 min, 30 min, 1 hr and 24 hrs of the administration. A human HGF concentration in the muscles of rats was measured by using Immunis HGF EIA (prepared by Institute of Immunology) that is an ELISA kit for measuring human HGF. As for HGF in the organs, 20 mM Tris-HCl (pH 7.5) containing 2 M NaCl, 1 mM PMSF, 1 mM EDTA and 0.1% Tween 80 was used as an extracting solution, homogenized for a minute, and centrifuged for 60 min at 4° C. and 15,000 rpm, and an amount of HGF in the extracting solution was measured by using the ELISA kit described above. As for a standard solution, HGF of a known concentration was also added to the muscles of rats that were not subjected to the administration of HGF, and a solution containing HGF that was extracted in a similar manner was used. Regarding a sample diluent as well, an extracting solution for the organs of rats that were not subjected to the administration of HGF was similarly prepared for use. An analysis of change in concentration was conducted by using the moment analysis method.

(2) Result

Pharmacokinetic parameters obtained from results of measurements of human HGF concentration in the muscles are shown in Table 3. In the intravenous bolus administration, however, it should be noted that parameters were calculated for the administration of HGF at 0.01 mg/kg by assuming a linearity in relation to the doses for the purpose of comparison. If administration of the same dose of HGF were supposed, AUC in the muscles would be significantly high in the intramuscular administration (administration area) in comparison with that in the intravenous bolus administration at about 650 times of that in the intravenous bolus administration. The maximum concentration (Cmax) in the muscles would be also significantly high in the intramuscular administration (administration area) in comparison with that in the intravenous bolus administration at about 960 times of that in the intravenous bolus administration.

TABLE 3

| | Intramuscular (im) | Intravenous bolus (iv) | im/iv |
|---|---|---|---|
| AUC (ng•hr/g muscle) | 4160 | 6.37 | 650 |
| Cmax (ng/g muscle) | 459 | 0.476 | 960 |

Example 2

Study of the Efficacy by Intramuscular Administration to Rat ASO Model of Hinlimb Ischemia (1) Method SD rats (9 weeks old, male) were used. The rats were anesthetized by intraperitoneal administration of about 50 mg/kg of pentobarbital (Nembutal U prepared by Dynabot). The left femoral artery was removed after ligation of branches, and rat ASO model of hindlimb ischemia was produced. The rats were etherized, and HGF or a vehicle was administered intramuscularly to a medial side of the left thigh. The administration was commenced immediately after removal of the femoral artery, and conducted at a dose of 1 mg/kg/day, a volume of 1 mL/kg/day and a frequency of once a day for 5 days. As the vehicle, 10 mM Na-citrate buffer (pH 5.5) containing 0.3 M NaCl, 0.03% Tween 80 and 5 mg/mL alanine was used. After 14 days of removal of the femoral artery, the rats were anesthetized by using pentobarbital, and depilated in the vicinity of the hindlimb by using a depilatory cream, and, by using the thermography (Avionics Japan), surface temperatures of skin were measured simultaneously for both hindlimbs at six locations, that is, a medial location of lower part of the thigh (Location 1 of FIG. 5), a medial location of the cnemial region (Location 2), a lateral location below knee (Location 3), a lateral location of anterior part of the cnemial region (Location 4), a lateral location in lower part of the thigh (Location 5) and a lateral location of the cnemial region (Location 6). For the respective measurement locations, a difference between surface temperatures of the skin was calculated by subtracting a temperature in the normal limb from that in the ischemic limb.

(2) Result

Figure 5:
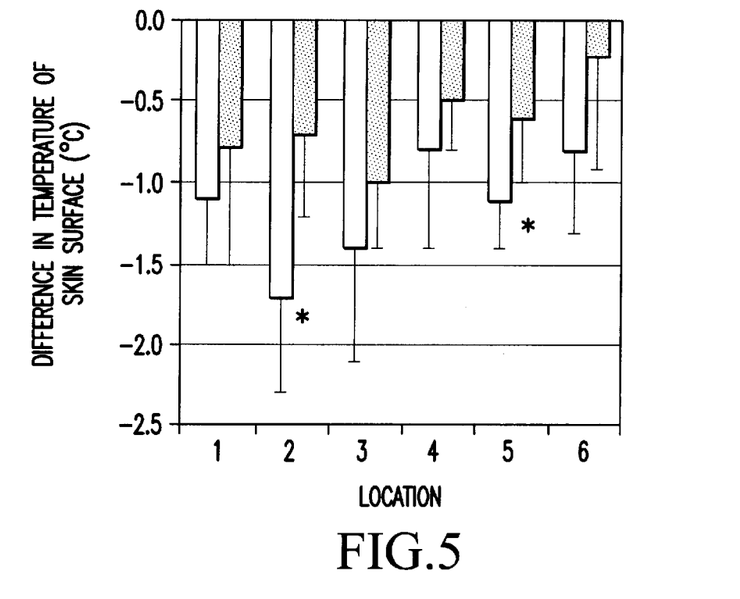
FIG. 5 is a graph showing an improving effect of HGF in relation to a surface temperature of skin in a rat model of hindlimb ischemia. The black bars represent HGF administration group and the white bars represent Vehicle administration group. Location 1 is the medial location of lower part of the thigh, location 2 is the medial location of the cnemial region, location 3 is the lateral location below knee, location 4 is the lateral location of anterior part of the cnemial region, location 5 is the lateral location in lower part of the thigh, and location 6 is the lateral location of the cnemial region.

Differences between surface temperatures of the skin of the ischemic limb and the normal limb are shown in FIG. 5. Thus, in a group subjected to removal of the femoral artery and administration of the vehicle (white in the figure), it was found that the temperatures were 0.8 to 1.7° C. lower at every location of the ischemic limb comparing with that of the normal limb. In contrast, in the HGF administration group (black in the figure), reduction in temperature was limited to 0.2 to 1.0° C. When the reduction in temperature at each location was compared between two groups, it was found that the reduction in temperature tended to be lower in the HGF administration group at all six locations. At two locations, that is, the medial location of the cnemial region and the lateral location in lower part of the thigh, the reduction in temperature was significantly restricted by the administration of HGF.

As shown in FIG. 5, when rat model of hindlimb ischemia was produced, and HGF was administered intramuscularly to femoral region of the ischemic limb, the reduction in surface temperature of the skin in the ischemic limb was restricted. It is considered that the circulation kinetics in the ischemic limb was improved by the angiogenic effect of HGF, and the reduction in temperature was thereby suppressed.

Example 3

Effects of Chondroitin Sulfate In Vitro Release of HGF from Minipellets Containing HGF (1) Method of Preparing Minipellets Containing HGF with a Content of 10% of Alanine Content of HGF: 131.2 µg/mg minipellet An aqueous solution of 6.9 mL containing 65.3 mg of HGF, 4.4 mL of an aqueous solution containing 1% alanine, 16 mL of distilled water and 16.7 g of 2% atelocollagen were mixed, and freeze-dried, then swelled by adding a small quantity of distilled water, and kneaded to make a homogenous liquid mixture. The mixture was placed in a disposable syringe of 10 mL, and centrifuged for 60 min at 10,000 G for degassing. By drying and cutting the mixture after it was extruded from the syringe, a cylindrical minipellet (1.1 mm in diameter and 4 mm in length) containing 500 µg of HGF in each cylinder was obtained.

(2) Method of Preparing Minipellets Containing HGF with a Content of 10% of Chondroitin Sulfate Content of HGF: 132.8 µg/mg Minipellet An aqueous solution of 6.9 mL containing 65.3 mg of HGF, 2.9 mL of an aqueous solution containing 1.5% chondroitin sulfate, 17 mL of distilled water and 16.7 g of 2% atelocollagen were mixed, and freeze-dried, then swelled by adding a small quantity of distilled water, and kneaded to make a homogenous liquid mixture. The mixture was placed in a disposable syringe of 10 mL, and centrifuged for 60 min at 10,000 G for degassing. By drying and cutting the mixture after it was extruded from the syringe, a cylindrical minipellet (0.9 mm in diameter and 4 mm in length) containing 500 µg of HGF in each cylinder was obtained.

(3) In Vitro Release Test

PBS (pH 7.4) containing 0.3% Tween 20 was used as a releasing solution. At 37° C., the minipellet prepared by the above-described method was placed in the releasing solution of 2 mL, and a releasing rate of HGF was measured (n=2). An HGF concentration in the releasing solution was measured by the heparin affinity chromatography.

Figure 6:
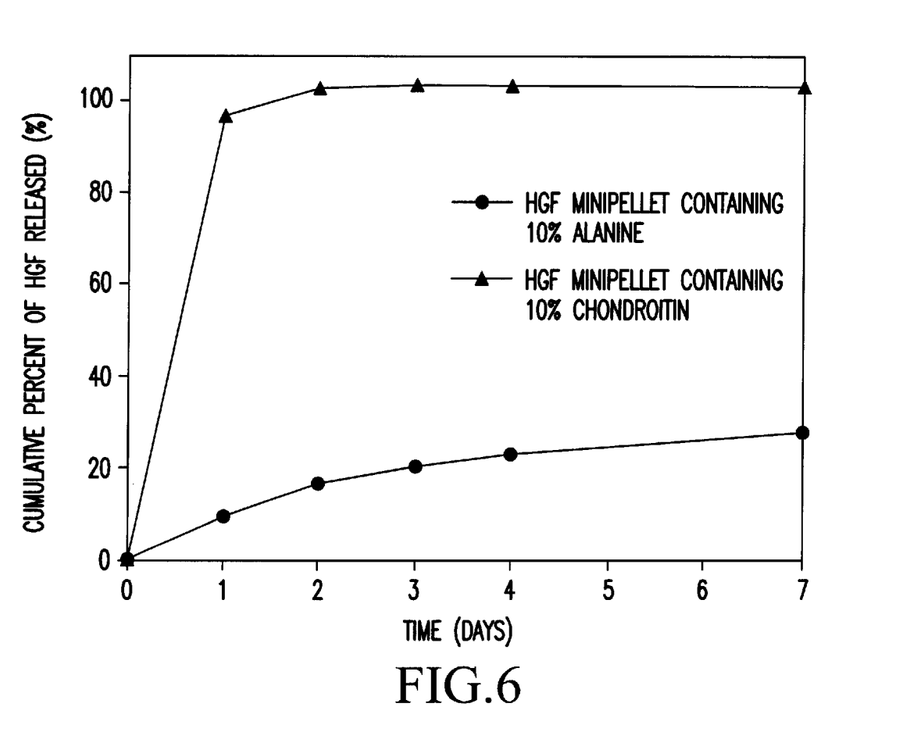
FIG. 6 is a figure showing release of HGF from a minipellet of collagen containing HGF.

A result of the experiment is shown in FIG. 6. Thus, HGF of about 100% was released from the minipellet containing chondroitin sulfate after a day, while HGF was slowly released from the minipellet containing alanine with no content of chondroitin sulfate. Even after seven days, an amount of HGF released was less than 30% of the content in the minipellet. It shows that release of HGF can be accelerated by allowing such proteoglycan as chondroitin sulfate that has an affinity to HGF to be contained together with HGF. To the contrary, it represents that the release can be slower, and HGF can be allowed to locally act on an administration region by allowing no such proteoglycan as chondroitin sulfate to be contained together with HGF.

Example 4

Phosphorylation of c-MET in Organs after Intramuscular Administration of HGF to Rats (1) Method By using SD rats (12 weeks old, male), phosphorylation of c-Met in muscles, liver and kidney after intramuscular administration was studied. Under ether anesthesia of the rats, 3, 0.3 or 0.03 mg/kg HGF was administered to a posterior muscle of the left thigh of rats. After 5 min and 30 min of the administration, the rats were exsanginated, and the muscles, liver and kidney were removed. A RIPA buffer (50 mM Tris-HCl (pH 7.4) containing 50 mM NaCl, 1% Triton X-100, 5 mM EDTA, 10 mM $Na_4P_2O_7$, 50 mM NaF, 1 mM $Na_3VO_4$, 0.4 mM AEBSF, 10 µg/mL leupeptin, 10 µg/mL aprotinin and 1 µg/mL pepstatin A) of 5 (muscles) or 8 (liver and kidney) mL/g tissue was added to the organs removed, and homogenization was conducted by using polytron. Then, precipitates were removed by centrifugation for 30 min at 16,000 rpm and 4° C. An extracting solution containing 10 mg (muscles) or 5 mg (liver and kidney) of protein was added to the RIPA buffer to make 1 mL of solution, and Protein G Sepharose (prepared by Pharmacia) of 50 µl (about 50%) was added thereto, which was then mixed for 2 hrs at 4° C. The Protein G Sepharose was removed by centrifugation, and anti-c-Met antibody (prepared by Santa Cruz) of 1 µg was added to a supernatant fluid of the solution, which was then mixed for a night at 4° C. Further, Protein G Sepharose of 20 µl was added to the solution, and the solution was subjected to mixing for 2 hrs at 4° C. A supernatant fluid was removed by centrifugation, the Protein G Sepharose was washed three times by using the RIPA buffer of 1 mL, then 2× loading buffer were added, and the solution was heated at 100° C. for 5 min, and subjected to SDS-PAGE of 7.5%. Migration proteins were electrically transferred and bound onto a nitrocellulose filter. The filter was blocked by shaking it in TBS-T (10 mM Tris-HCl (pH 7.6) containing 150 mM NaCl and 0.05% Tween 20) containing 3% BSA. After slightly washing the filter by using TBS-T, the filter was shaken in TBS-T containing 1 µg/mL of anti-phosphotyrosine antibody (prepared by Upstate Biotechnology) at room temperature for an hour. The filter was further washed by using TBS-T, and shaken thereafter for an hour at room temperature in TBS-T containing peroxydase-labeled anti-mouse Ig antibody (prepared by Amersham) that was diluted to 2000 times. After washing the filter by using TBS-T, detection of phosphorylated c-Met was conducted by using an ECL western blotting reagent (prepared by Amersham).

The filter was deprobed by shaking it in a solution containing 62.5 mM Tris-HCl (pH 6.7), 100 mM 2-mercaptoethanol and 2% SDS for 30 min at 60° C., and washed by using TBS-T, then blocked in TBS containing 3% BSA. The filter was further washed slightly, then shaken in TBS-T containing 0.5 µg/mL of anti-c-Met antibody for an hour at room temperature. It was then further washed by using TBS-T, and shaken for an hour at room temperature in TBS-T containing peroxydase-labeled anti-mouse Ig antibody (prepared by Amersham) that was diluted to 2000 times. After washing the filter by using TBS-T, detection of c-Met was conducted by using an ECL western blotting reagent (prepared by Amersham).

(2) Result

Figure 7:
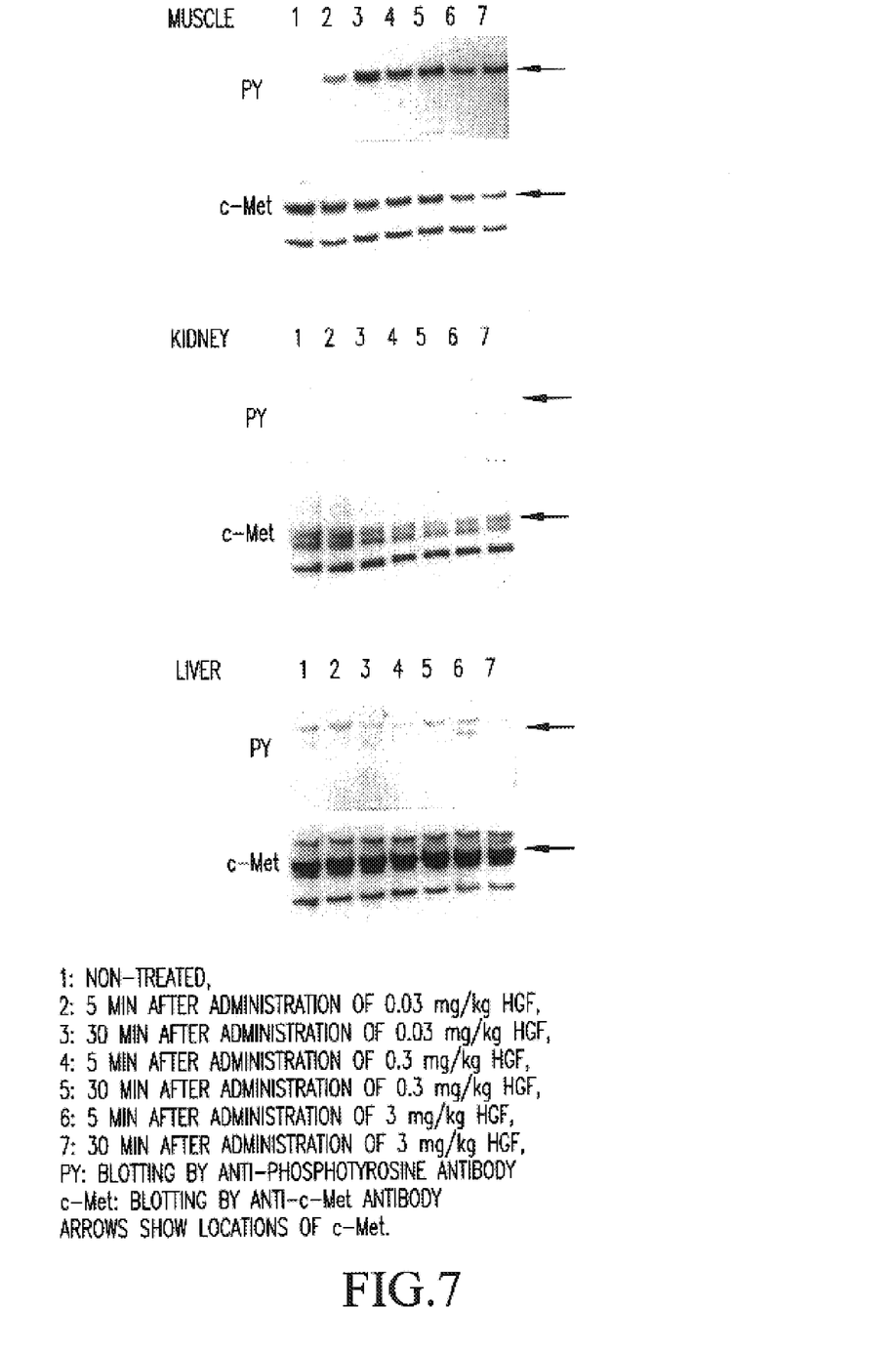
FIGS. 7A–7C are figures showing phosphorylation of c-Met in a muscle, liver and kidney after administration of HGF to a muscle of femoral region of a rat.

A result of IP-Western test on phosphorylated c-Met is shown in FIG. 7. In muscular tissues, significant phosphorylation of c-Met was observed at doses 0.03 to 3 mg/kg. On the other hand, in the liver and kidney, phosphorilation of c-Met by the intramuscular administration of HGF was undetected. It shows that HGF can be allowed to selectively act on muscular tissues and blood vessels in the muscular tissues without affecting the liver and kidney by intramuscular administration of HGF at a dose of 3 mg/kg or less.

Example 5

Study (1) of the Efficacy of Intramuscular Administration to Rat ASO Model of Hindlimb Ischemia (1) Method SD rats (14 weeks old, male) were used. The rats were anesthetized by intraperitoneal administration of about 50 mg/kg of pentobarbital (Nembutal prepared by Dynabot). The left femoral artery was removed after ligation of branches, and rat ASO model of hindlimb ischemia was produced (see Cardiovascular Research, 35, 547–552 (1997)). HGF or a vehicle was administered intramuscularly to the left femoral region immediately thereafter. A dose of 10 µg/kg and an amount of administration of 1 mL/kg were used. After 4 days, a further administration was conducted in a similar manner by etherizing the rats. As the vehicle, 10 mM Na-citrate buffer (pH 5.5) containing 0.3 M NaCl, 0.03% Tween 80 and 5 mg/mL alanine was used. After 14 days of removal of the femoral artery, the rats were anesthetized by using pentobarbital, and the blood pressure in the hindlimb was measured by using a noninvasive blood pressure monitor for experimental animals. The I/N ratio (%)= blood pressure in an ischemic limb/blood pressure in a normal limb×100 was calculated from respective blood pressures of the normal limb and ischemic limb, and evaluated.

(2) Result

Figure 8:
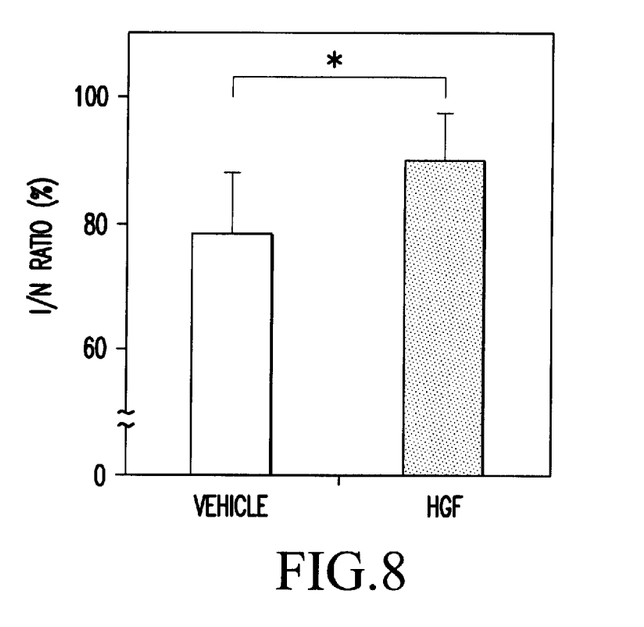
FIG. 8 is a figure showing a result of determination of the I/N ratio (%) (blood pressure in an ischemic limb/blood pressure in a normal limb×100) by intramuscularly administering HGF to a rat ASO model of hindlimb ischemia.

A result is shown in FIG. 8. In the HGF administration group, the I/N ratio was significantly improved in comparison with the vehicle administration group. It was considered to be caused by an angiogenic effect of HGF.

Example 6

Study of the Efficacy of Intramuscular Administration to Rabbit ASO Model of Hindlimb Ischemia (1) Method NZW rabbits (22 weeks old, male) were used. The rabbits were anesthetized by intramuscular administration of 5 mg/kg of xylazine (Seractal prepared by Bayer Ltd.) and 50 mg/kg of ketamine (Ketalar prepared by Sankyo Co., Ltd.) to the brachial region. Rabbit ASO model of hindlimb ischemia was produced by dissectioning a left femoral region, and removing a left femoral artery (see J. Clin. Invest., 93, 662–670 (1994)). After 10 days and 15 days thereof, the rabbits were anesthetized in a similar manner, and HGF or a vehicle was intramuscularly administered to the left femoral region. A dose of 100 µg/kg and an amount of administration of 1 mL/kg were used. As the vehicle, 10 mM Na-citrate buffer (pH 5.5) containing 0.3 M NaCl, 0.03% Tween 80 and 5 mg/mL alanine was used. After 10 (before administration of the drug), 22 and 42 days from the removal of femoral artery, the rabbits were anesthetized by the above-described method, and blood pressures of both hindlimbs were measured by using a Doppler blood flowmeter (prepared by Triton) and a mercurial blood pressure gauge. The I/N ratio (%)=blood pressure in an ischemic limb/blood pressure in a normal limb×100 was calculated from blood pressures in the normal limb and ischemic limb, and evaluated. The ratio of increase of the I/N ratio from after 10 days was also calculated, and evaluated. After 10 days from the removal of artery and on the final day (after 41 or 42 days), the angiography was conducted selectively for the left hindlimb by using a contrast medium (Optiray 350 prepared by Yamanouchi Pharmaceutical Co., Ltd.). An angiographic score was determined by placing a sheet with an alignment of circles of 2.5 mm in diameter over the angiogram obtained, counting the number of circles that overlap a blood vessel, and calculating the ratio to the total number (800) of circles. The increase ratio (%) of the angiographic score from that after 10 days from the removal of blood vessel to that of the final day was calculated for each rabbit, and evaluated as the increase ratio of angiographic score. On the final day, a degree of arthrosclerosis of the ischemic limb, presence or absence of necrosis and autoamputation of the toe and ulceration in the crus of the ischemic limb were observed.

(2) Result

Figure 9:
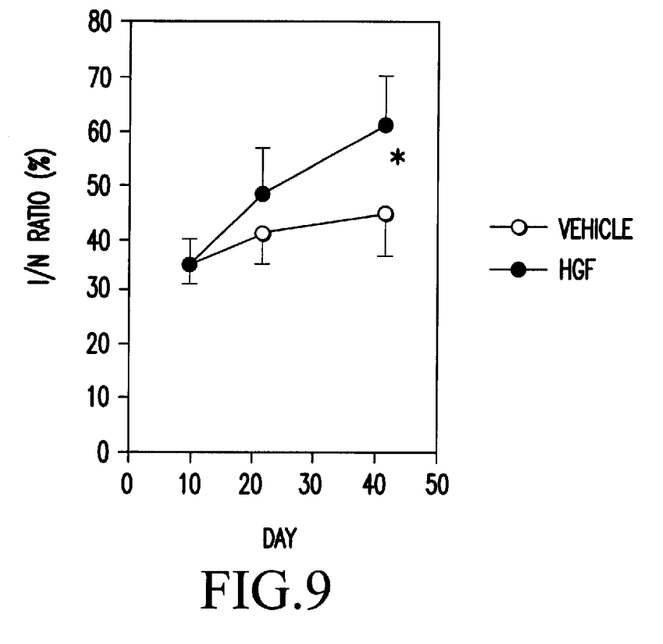
FIG. 9 is a figure showing a result of determination of change in the I/N ratio of the blood pressure in hindlimbs by intramuscularly administering HGF to a rabbit ASO model of hindlimb ischemia.
Figure 10:
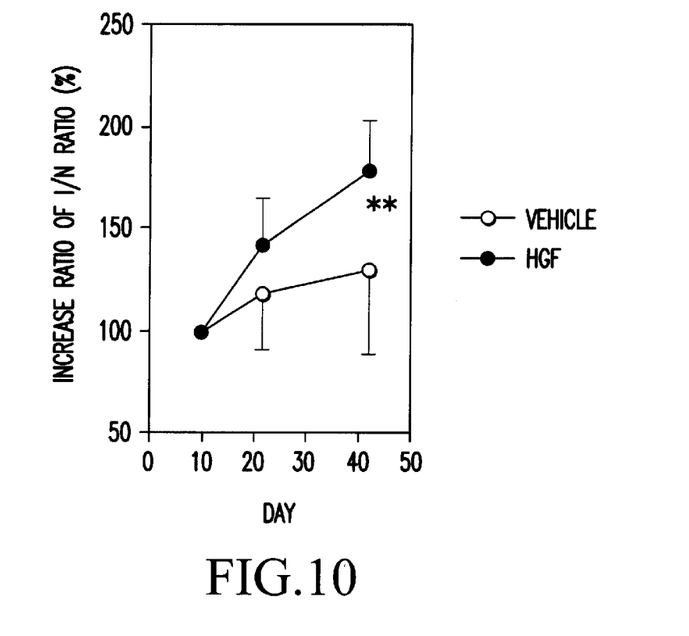
FIG. 10 is a figure showing a result of determination of the increase ratio in the I/N ratio of the blood pressure in hindlimbs by intramuscularly administering HGF to a rabbit ASO model of hindlimb ischemia.
Figure 11:
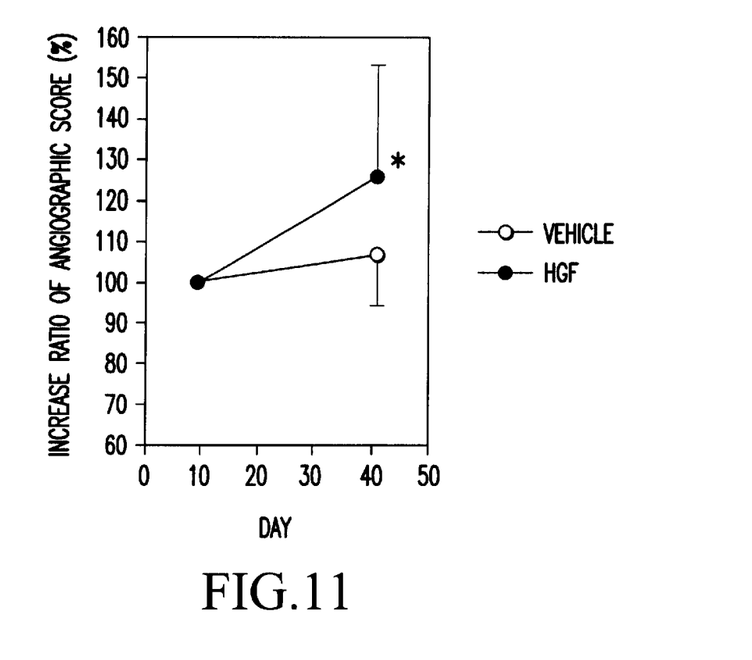
FIG. 11 is a figure showing a result of determination of the increase ratio in angiographic score by intramuscularly administering HGF to a rabbit ASO model of hindlimb ischemia.

Change of the I/N ratio of blood pressure in the hindlimbs is shown in FIG. 9. The ratio tended to be at a high value in the HGF administration group after 22 days from the removal of artery, and the I/N ratio was significantly improved in the HGF administration group after 42 days in comparison with the vehicle administration group. It was considered that the blood circulation kinetics was improved in the ischemic limb by the angiogenesis of HGF. The increase ratio of the I/N ratio of blood pressure in the hindlimbs is shown in FIG. 10. The increase ratio of the I/N ratio from 10 days to 42 days after the removal of artery was significantly high in the HGF administration group in comparison with that of the vehicle group. The increase ratio of angiographic score is shown in FIG. 11. The increase ratio was significantly high in the HGF administration group in comparison with that of the vehicle administration group, and it was considered that development of collateral vessels was accelerated by an effect of HGF. Also, in observation of the ischemic limb conducted on the final day of evaluation, it was recognized that symptoms were minor in the HGF administration group in comparison with the vehicle administration group (Table 4), and it was supposed that improvement of blood circulation kinetics in the ischemic limb by the administration of HGF was reflected thereby.

TABLE 4

| Group | Arthrosclerosis of hindlimb | | | Necrosis and autoamputation of toe | Ulceration in ischemic hindlimb |
|---|---|---|---|---|---|
| | None | Minor | Major | | |
| vehicle (n = 8) | 4 | 1 | 3 | 1 | 3 |
| HGF (n = 8) | 6 | 2 | 0 | 0 | 0 |

Example 7

Study (2) of the Efficacy of Intramuscular Administration to Rat ASO Model of Hindlimb Ischemia (1) Method SD rats (14 weeks old, male) were used. The rats were anesthetized by intraperitoneal administration of about 50 mg/kg of pentobarbital (Nembutal prepared by Dynabot). The left femoral artery was excised after ligation of branches, and rat ASO model of hindlimb ischemia was produced (see Cardiovascular Research, 35, 547–552 (1997)). HGF or a vehicle was administered intramuscularly to the left femoral region immediately thereafter.

A dose of 1 µg/kg and an amount of administration of 1 mL/kg were used for all experiments. After 4 days, a second administration was conducted in a similar manner by etherizing the rats As the vehicle, 10 mM Na-citrate buffer (pH 5.5) containing 0.3 M NaCl, 0.03% Tween 80 and 5 mg/mL alanine was used. After 7 days of removal of the femoral artery, the rats were anesthetized by using pentobarbital, and the blood pressure in the hindlimb was measured by using a noninvasive blood pressure monitor for experimental animals The I/N ratio (%)=blood pressure in an ischemic limb/blood pressure in a normal limb ×100 was calculated from respective blood pressures of the normal limb and ischemic limb, and evaluated.

Additionally, in order to study an effect of a single administration, a similar experiment was conducted by conducting the administration only on the day of excision of the femoral artery. An amount of administration of HGF was 3 µg/kg.

(2) Result

Figure 12:
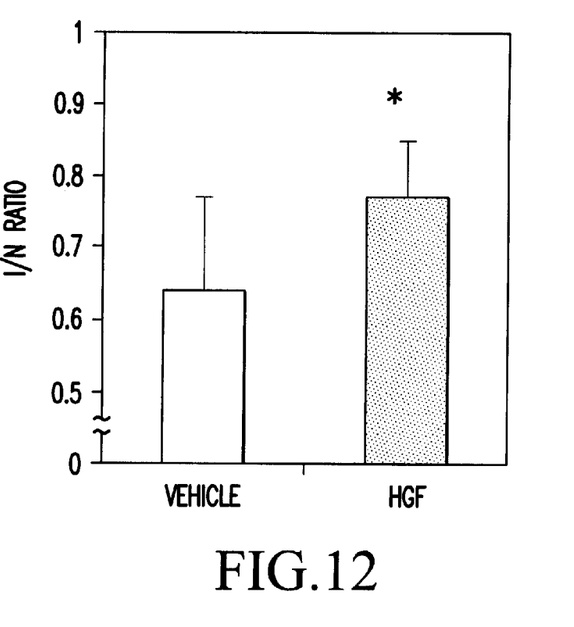
FIG. 12 is a figure showing a result of determination of the I/N ratio by intramuscularly administering (1 μg/kg×twice) to a rat ASO model of hindlimb ischemia.

A result of two administrations is shown in FIG. 12. Seven days after the removal of femoral artery, the I/N ratio was significantly improved in the HGF administration group in comparison with that of the vehicle administration group. It was considered to be caused by an angiogenic effect of HGF. It is found that HGF is effective at low dose of 1 µg/kg× twice.

Figure 13:
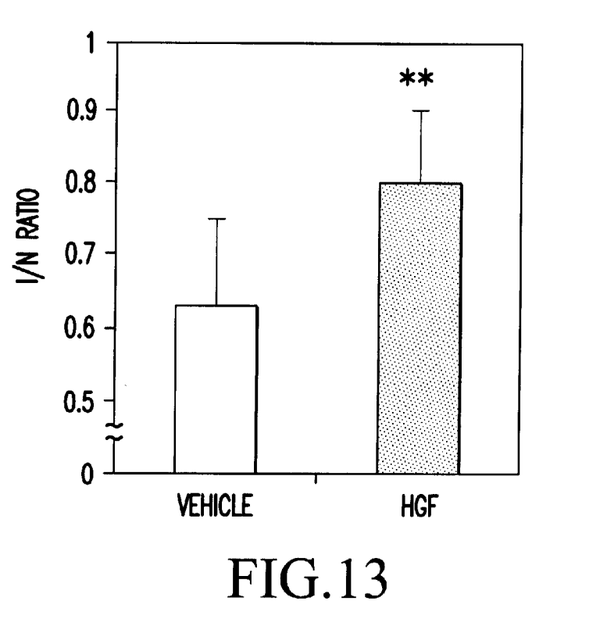
FIG. 13 is a figure showing a result of determination of the I/N ratio by intramuscularly administering (3 μg/kg×single) to a rat ASO model of hindlimb ischemia.

A result of a single administration is shown in FIG. 13. Seven days after the removal of femoral artery, the I/N ratio was significantly improved in the HGF administration group in comparison with that of the vehicle administration group. It shows that HGF is effective even when it is administered once.

Pharmaceutical Example 1

A freeze-dried preparation was obtained by preparing a sterile solution containing 1 mg HGF, 1 g mannitol and 10 mg polysorbate 80 in 100 mL saline, and dividing it to separate vials 1 mL each, then subjecting it to freeze-drying and sealing.

Pharmaceutical Example 2

A freeze-dried preparation was obtained by preparing a sterile solution containing 1 mg HGF and 100 mg human serum albumin in 100 mL of 0.02 M phosphate buffer (containing 0.15 M NaCl and 0.01% polysorbate 80, pH 7.4), and dividing it to separate vials 1 mL each, then subjecting it to freeze-drying and sealing.

INDUSTRIAL APPLICABILITY

According to the invention, preparations to be administered for treating or preventing ischemic diseases or arterial diseases which contain HGF as an active ingredient can be provided. The preparations for intramuscular administration according to the invention has such effect that it achieves reduction of a dose in comparison with conventional intravenous administration, and less affects other organs except an affected region, because it has a half-life longer than that of the intravenous administration, and can be easily retained in a muscle.

What is claimed is:

1. A method for treating ischemic disease of heart or limbs in a patient in need thereof, comprising:

intramuscularly administering to a patient suffering from said ischemic disease, an effective amount of a composition comprising Hepatocyte Growth Factor (HGF) as an active ingredient, wherein the composition is transported to, distributed in, and acts on tissues that are local to or around the region of administration, wherein a maximum concentration of said composition in the blood, liver and kidney is a hundredth or less, and a concentration in said muscle is at least 50 times greater than when said composition is administered by intravenous bolus administration, and wherein the composition has reduced transportation to, distribution in, and effect in blood or bodily organs other than those that are local to said region of administration, thereby treating said ischemic disease of heart or limbs.

2. A method for treating ischemic disease of heart or limbs in a patient in need thereof, comprising:

intramuscularly administering to a patient suffering from said ischemic disease, an effective amount of a composition comprising Hepatocyte Growth Factor (HGF) as an active ingredient, wherein the composition is transported to, distributed in, and acts on tissues that are local to or around the region of administration, wherein AUC in the blood, liver and kidney is a fifth or less, and AUC in said muscle is at least 50 times greater than when said composition is administered by intravenous bolus administration, and wherein the composition has reduced transportation to, distribution in, and effect in blood or bodily organs other than those that are local to said region of administration, thereby treating said ischemic disease of heart or limbs.

3. A method for treating ischemic disease of heart or limbs in a patient in need thereof, comprising:

intramuscularly administering to a patient suffering from said ischemic disease, an effective amount of a composition comprising Hepatocyte Growth Factor (HGF) as an active ingredient, wherein the composition is transported to, distributed in, and acts on tissues that are local to or around the region of administration and wherein said composition is administered at a dose of is 0.1 to 10 µg/kg, and wherein the composition has reduced transportation to, distribution in, and effect in blood or bodily organs other than those that are local to said region of administration, thereby treating said ischemic disease of heart or limbs.

* * * * *